United States Patent
Hyuga

(10) Patent No.: US 9,585,630 B2
(45) Date of Patent: Mar. 7, 2017

(54) ULTRASONIC MEASUREMENT APPARATUS AND ULTRASONIC MEASUREMENT METHOD

(71) Applicant: SEIKO EPSON CORPORATION, Tokyo (JP)

(72) Inventor: Takashi Hyuga, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 63 days.

(21) Appl. No.: 14/620,899

(22) Filed: Feb. 12, 2015

(65) Prior Publication Data

US 2015/0238163 A1    Aug. 27, 2015

(30) Foreign Application Priority Data

Feb. 27, 2014 (JP) ................ 2014-036406

(51) Int. Cl.
  *A61B 8/00* (2006.01)
  *A61B 8/08* (2006.01)
  *A61B 8/14* (2006.01)

(52) U.S. Cl.
  CPC ............ *A61B 8/085* (2013.01); *A61B 8/0891* (2013.01); *A61B 8/5223* (2013.01); *A61B 8/0858* (2013.01); *A61B 8/14* (2013.01)

(58) Field of Classification Search
  CPC ................ A61B 8/08; A61B 8/14; A61B 5/05
  See application file for complete search history.

(56) References Cited

U.S. PATENT DOCUMENTS

| 2004/0059220 | A1* | 3/2004 | Mourad | A61B 5/0048 600/442 |
| 2009/0105589 | A1* | 4/2009 | Osaka | A61B 8/06 600/443 |
| 2010/0217125 | A1* | 8/2010 | Kadokura | A61B 5/02007 600/443 |
| 2011/0040181 | A1 | 2/2011 | Yokota et al. | |

FOREIGN PATENT DOCUMENTS

JP    2009-066268 A    4/2009

\* cited by examiner

*Primary Examiner* — Joel Lamprecht
(74) *Attorney, Agent, or Firm* — Oliff PLC

(57) ABSTRACT

An ultrasonic measurement apparatus detects a plurality of feature points in a B-mode image acquired by ultrasonic measurement. The feature point detection is repeatedly performed for each measurement frame. Then, a displacement vector of each feature point between measurement frames that are temporally adjacent (consecutive) to each other is calculated. Then, a displacement direction is calculated based on the displacement vector for each feature point. An intersection of the displacement direction lines is detected as a cross-sectional center position of a blood vessel.

7 Claims, 6 Drawing Sheets

ULTRASONIC MEASUREMENT APPARATUS AND ULTRASONIC MEASUREMENT METHOD

BACKGROUND

1. Technical Field

The present invention relates to an ultrasonic measurement apparatus that detects a blood vessel position using an ultrasonic wave.

2. Related Art

As an example of measuring biological information using an ultrasonic wave, the evaluation of a vascular function including the determination of a vascular disease is performed. For example, the intima media thickness (IMT) of the carotid artery, which is an indicator of arteriosclerosis, is measured. In such measurement, the position or shape of a blood vessel of the tissue in the body is measured.

JP-A-2009-66268 discloses a technique of estimating and modeling the position or shape of the carotid artery based on a B-mode image that is a cross-sectional image of the carotid artery. In this technique, focusing on the movement of the artery due to beating of the heart, generation of an evaluation function of a model, optimization for estimating the position or shape of the carotid artery of the next frame, and modeling are repeated for each frame.

In the technique disclosed in JP-A-2009-66268, since the generation of an evaluation function, optimization, and modeling are repeatedly performed for each frame, calculation processing related to measurement becomes complicated. Accordingly, there has been a problem in that the amount of calculation is increased.

SUMMARY

An advantage of some aspects of the invention is to propose a new technique for detecting the position of a blood vessel to be subjected to ultrasonic measurement.

A first aspect of the invention is directed to an ultrasonic measurement apparatus including: a measurement data acquisition unit that transmits an ultrasonic wave to a surface of a body and acquires measurement data, which is obtained by measuring a cross section of the body with the ultrasonic wave, based on a received signal; a displacement detection unit that detects displacement of a tissue in the body based on the measurement data; and a blood vessel position detection unit that detects a blood vessel position in the body based on the detected displacement.

As another aspect of the invention, the first aspect of the invention may be configured as an ultrasonic measurement method including: transmitting an ultrasonic wave to a surface of a body and acquiring measurement data, which is obtained by measuring a cross section of the body with the ultrasonic wave, based on a received signal; detecting displacement of a tissue in the body based on the measurement data; and detecting a blood vessel position in the body based on the detected displacement.

According to the first aspect and the another aspect of the invention, a blood vessel position in the body is detected based on the displacement of the tissue in the body that has been detected based on the measurement data obtained by measuring the cross section of the body with an ultrasonic wave. A blood vessel repeats contraction and relaxation periodically according to beating, and a tissue in the body around the blood vessel is also displaced in synchronization with the periodic contraction and relaxation of the blood vessel. Therefore, it is possible to realize a new technique for detecting the blood vessel position that has caused the displacement by detecting the displacement of the tissue in the body.

A second aspect of the invention is directed to the ultrasonic measurement apparatus according to the first aspect of the invention, wherein the displacement detection unit detects the displacement by comparing a plurality of pieces of measurement data in time series.

According to the second aspect of the invention, it is possible to detect the displacement of the tissue in the body by comparing a plurality of pieces of measurement data in time series.

A third aspect of the invention is directed to the ultrasonic measurement apparatus according to the first or second aspect of the invention, wherein the displacement detection unit detects a displacement direction of the tissue in the body, and the blood vessel position detection unit detects the blood vessel position based on the displacement direction.

According to the third aspect of the invention, the displacement direction of the tissue in the body is detected, and the blood vessel position is detected based on the displacement direction. Since the blood vessel repeats isotropic contraction and relaxation on the cross section in the short-axis direction of the blood vessel, the displacement direction of the blood vessel or the tissue in the body around the blood vessel becomes a radial direction from the approximate center position of the short-axis cross section of the blood vessel. Therefore, it is possible to detect the blood vessel position from the detected displacement direction of the tissue in the body.

A fourth aspect of the invention is directed to the ultrasonic measurement apparatus according to any one of the first to third aspects of the invention, wherein the ultrasonic measurement apparatus further includes a feature point detection unit that detects a plurality of feature points relevant to the tissue in the body based on the measurement data, the displacement detection unit detects displacement directions of the plurality of feature points, and the blood vessel position detection unit detects the blood vessel position by calculating an intersection of lines of the displacement directions of the plurality of feature points.

According to the fourth aspect of the invention, the blood vessel position is detected by calculating the intersection of the displacement direction lines of the plurality of feature points relevant to the tissue in the body. Since the blood vessel repeats isotropic contraction and relaxation on the cross section in the short-axis direction of the blood vessel, an intersection of the displacement direction lines of the plurality of feature points can be detected as the approximate center position of the short-axis cross section of the blood vessel.

A fifth aspect of the invention is directed to the ultrasonic measurement apparatus according to the fourth aspect of the invention, wherein the feature point detection unit detects a feature point relevant to the blood vessel or a tissue in the body around the blood vessel.

According to the fifth aspect of the invention, a feature point relevant to the blood vessel or a tissue in the body around the blood vessel is detected as the feature point. Therefore, since it is possible to detect the displacement of each feature point according to the contraction and relaxation of the blood vessel, it becomes easy to detect the blood vessel position.

A sixth aspect of the invention is directed to the ultrasonic measurement apparatus according to any one of the first to fifth aspects of the invention, wherein the displacement detection unit detects the displacement according to at least one of contraction and relaxation of the blood vessel.

According to the sixth aspect of the invention, a displacement according to at least one of the contraction and relaxation of the blood vessel is detected as the displacement of the tissue in the body. Since the blood vessel repeats contraction and relaxation, the detected displacement direction of the tissue in the body can be represented by an approximately straight line. Therefore, by detecting the displacement according to at least one of the contraction and relaxation of the blood vessel, it is possible to detect the displacement direction of the tissue in the body.

BRIEF DESCRIPTION OF THE DRAWINGS

The invention will be described with reference to the accompanying drawings, wherein like numbers reference like elements.

DESCRIPTION OF EXEMPLARY EMBODIMENTS

Overall Configuration

Figure 1:
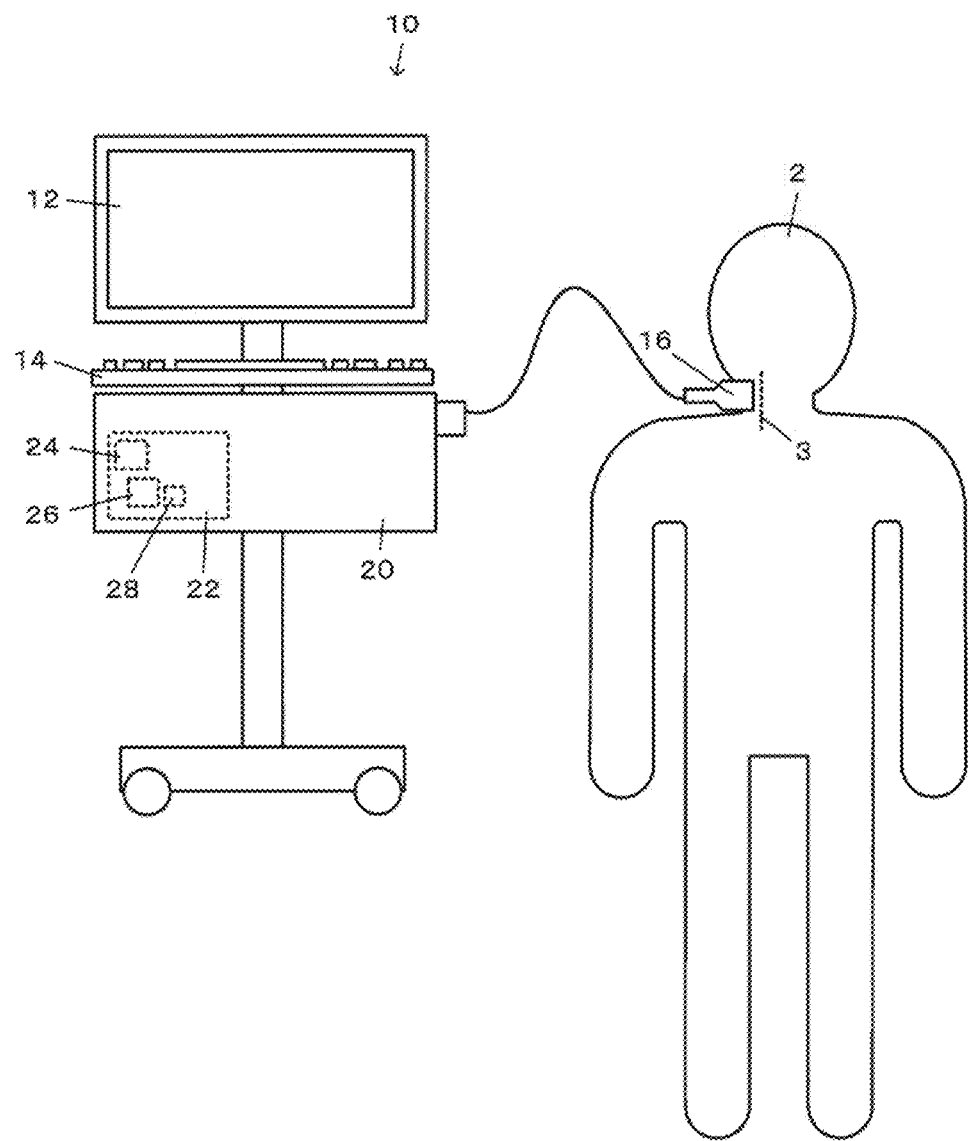
FIG. 1 is a diagram showing the overall configuration of an ultrasonic measurement apparatus.

FIG. 1 is a diagram showing an example of the configuration of an ultrasonic measurement apparatus 10 according to the present embodiment. The ultrasonic measurement apparatus 10 is an apparatus that measures biological information of a subject using an ultrasonic wave. In the present embodiment, vascular function information, such as the intima media thickness (IMT) of the carotid artery, is measured as biological information. Needless to say, it is also possible to measure other vascular function information, such as a blood vessel diameter or blood pressure measured from the blood vessel diameter, in addition to the IMT.

The ultrasonic measurement apparatus 10 includes a touch panel 12, a keyboard 14, an ultrasonic probe 16, and a main device 20. A control board 22 is mounted in the main device 20, and is connected to each unit, such as the touch panel 12, the keyboard 14, and the ultrasonic probe 16, so that signal transmission and reception therebetween are possible.

Not only various integrated circuits, such as a central processing unit (CPU) 24 and an application specific integrated circuit (ASIC), but also a storage medium 26, such as an IC memory or a hard disk, and a communication IC 28 for realizing data communication with an external device are mounted on the control board 22. The main device 20 realizes various functions according to the present embodiment, including ultrasonic measurement, by executing a control program stored in the storage medium 26 with the CPU 24 or the like.

Specifically, the main device 20 transmits or radiates an ultrasonic beam from the ultrasonic probe 16 to the tissue in the body of the subject 2 and receives the reflected wave. Then, by performing amplification and signal processing on a received signal of the reflected wave, it is possible to generate measurement data relevant to the structure in the body of the subject. Images of respective modes of a so-called A mode, B mode, M mode, and color Doppler mode are included in the measurement data. Measurement using an ultrasonic wave is repeatedly performed at predetermined periods. The measurement unit is referred to as a "frame".

The ultrasonic probe 16 is formed by arraying a plurality of ultrasonic transducers. In the present embodiment, ultrasonic transducers are arrayed in a row. However, it is possible to adopt a planar array configuration including a plurality of rows. Then, the ultrasonic probe 16 is fixed to the neck of the subject 2 in a relative posture in which an ultrasonic wave from each ultrasonic transducer traverses the carotid artery of the subject in a short-axis direction, and the biological information is measured.

Principle

Figure 2:
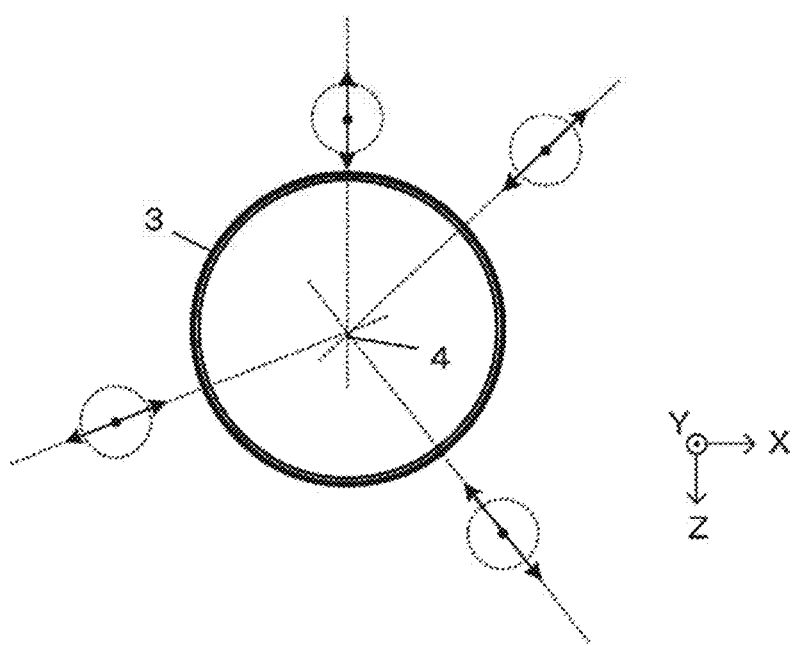
FIG. 2 is a diagram for explaining the contraction and relaxation of a blood vessel.

In measurement of vascular function information, a blood vessel position is detected first. FIG. 2 is a schematic diagram of a short-axis cross section of a blood vessel 3. The blood vessel 3 repeats isotropic contraction and expansion according to beating. The contraction and expansion direction is a radial direction from a center position 4 of the short-axis cross section of the blood vessel 3. Based on this, in the present embodiment, the displacement of the tissue in the body around the blood vessel 3 is detected using a B-mode image that is one type of measurement data, and a cross-sectional center position 4 of the blood vessel 3 is detected from the displacement direction. The dashed circle in FIG. 2 is some of feature points shown in FIG. 3, and the displacement direction of the center position of the dashed circle is indicated by the solid double-headed arrow.

An orthogonal three-dimensional coordinate system having a depth direction from the skin surface (body surface) as a Z axis, a longitudinal direction (blood flow direction) of the blood vessel 3 as a Y axis, and a short-axis direction of the blood vessel 3 perpendicular to the Y and Z axes as an X axis is used as a coordinate system in the present embodiment.

Figure 3:
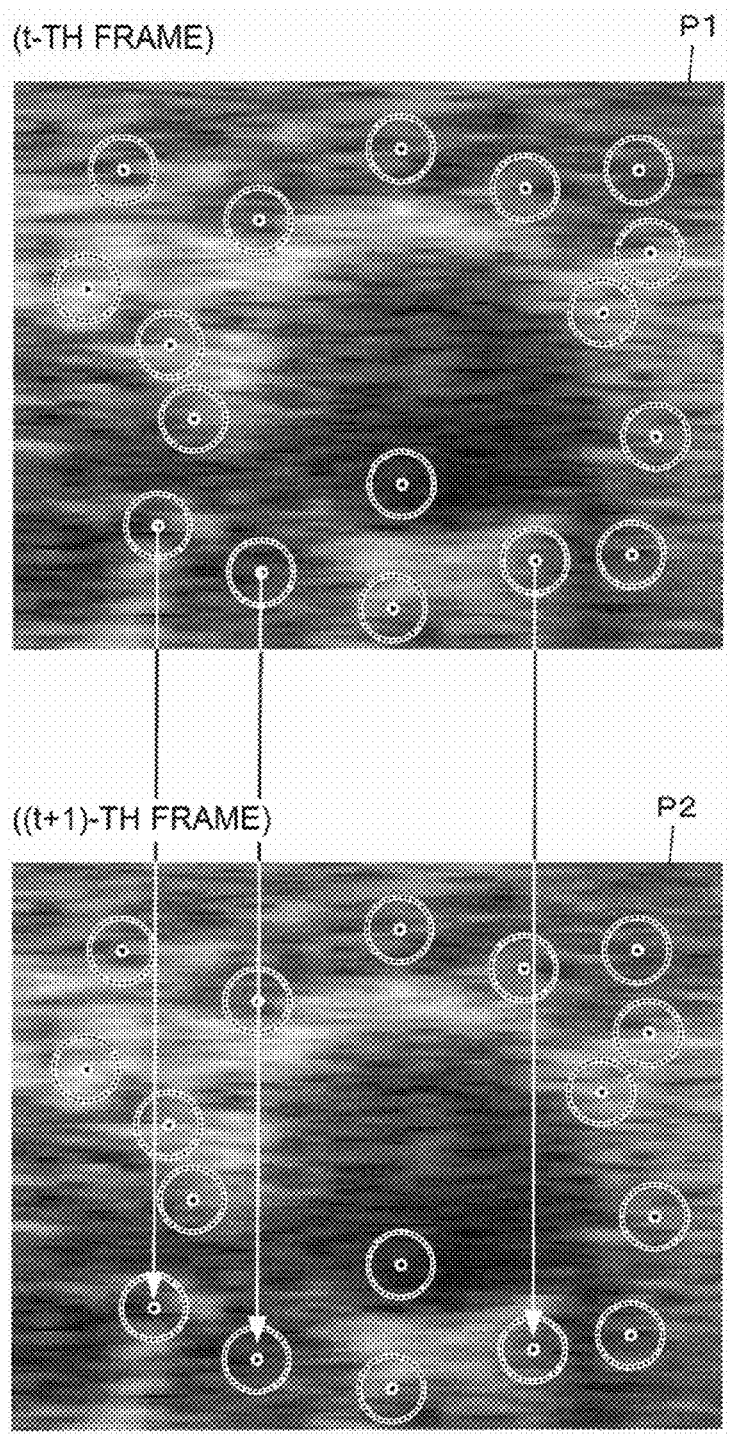
FIG. 3 is a diagram for explaining the calculation of a displacement vector.

More specific explanation will be given below. First, as shown in FIG. 3, feature points (center positions of the dashed circles in FIG. 3) in B-mode images P1 and P2 measured in two consecutive measurement frames are extracted, and feature point matching estimation (also referred to as tracking) between the two B-mode images P1 and P2 is performed. Feature points that could not be matched with each other are determined to be feature points having a small feature quantity and are deleted. Accordingly, only feature points whose positions with respect to the elapse of time can be specified (that is, tracked) are detected. Since the feature point extraction method and the matching estimation method can be realized by using known techniques appropriately, explanation thereof herein will be omitted.

Figure 4:
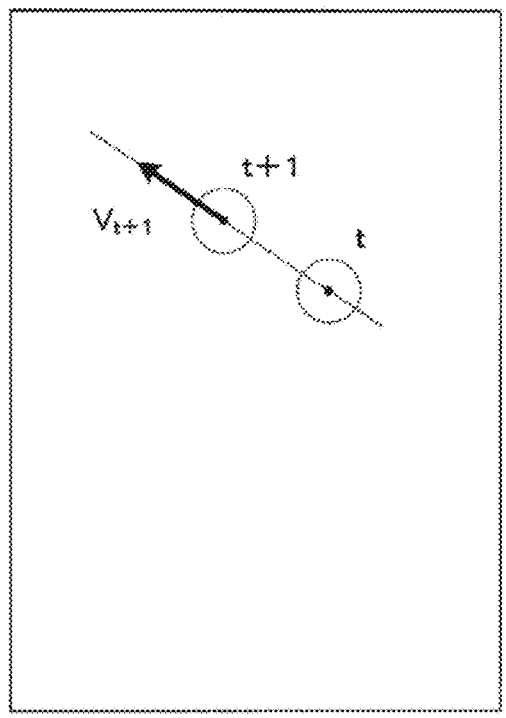
FIG. 4 is a diagram for explaining a method of determining the displacement direction.

Then, a displacement vector V indicating a position change between consecutive frames is calculated for each feature point detected as a feature point that can be tracked. FIG. 4 is a diagram showing an example of calculating a displacement vector $V_{t+1}$ based on the position of the t-th frame and the position of the next (t+1)-th frame for one certain detected feature point. The displacement vector V is calculated for each detected feature point.

Then, a direction of the displacement vector V is assumed to be the displacement direction of the feature point. In this case, in order to improve the detection accuracy of the blood vessel position, the displacement direction is determined for each feature point as follows. That is, the position of one feature point is tracked, and a plurality of displacement vectors V between a plurality of consecutive frames are calculated. Among the directions of the plurality of calculated displacement vectors V, the most frequently appearing direction is determined as the displacement direction of the feature point. That is, the direction determination is based on the majority method. By performing the direction determination for each feature point, the displacement direction of each feature point is determined.

Figure 5:
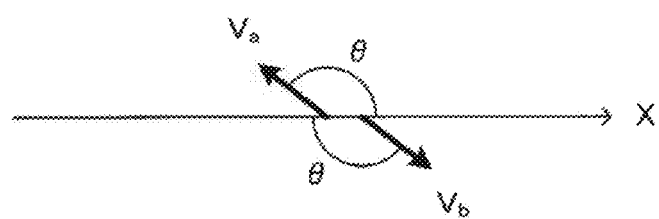
FIG. 5 is a diagram for explaining the detection of a feature point in a B-mode image.

For example, as shown in FIG. 5, a displacement direction is expressed as an angle θ between the displacement vector V and the X axis. Since the position of each feature point changes so as to reciprocate in the radial direction from the center of the blood vessel 3 as shown in FIG. 2, the angle θ is assumed to be in the range of "0° to 180°". That is, the displacement vectors V having opposite directions, such as displacement vectors shown in FIG. 5, are regarded as having the same displacement direction. Specifically, the displacement vector V is defined by position coordinates, a direction (also referred to as an orientation), and size. Therefore, if a counterclockwise angle (a clockwise angle is also possible) between the direction of the displacement vector V and the X-axis positive direction is in the range of "0° to 180°", the counterclockwise angle is determined as the angle θ of the displacement direction. If the counterclockwise angle between the direction of the displacement vector V and the X-axis positive direction is in the range of "180° to 360°", an angle obtained by subtracting 180° from the counterclockwise angle is determined as the angle θ of the displacement direction.

After the displacement direction of each of a plurality of feature points is determined, as shown in FIG. 2, a straight line (dotted line in FIG. 2) that passes through the position of each of the plurality of feature points and is in a direction along the displacement direction of each feature point is calculated (hereinafter, the straight line is referred to as a "displacement direction line"). Then, an intersection of the displacement direction lines is calculated, and the intersection of the displacement direction lines is set as the cross-sectional center position 4 of the blood vessel 3. Theoretically, the number of intersections calculated is 1. However, when a combination of two displacement direction lines is selected from a plurality of displacement direction lines and an intersection is calculated for each combination, the number of intersections calculated may not be 1. Therefore, among the intersections calculated for each combination of displacement direction lines, an intersection where the number of overlapping positions is the largest can be determined as the cross-sectional center position 4 of the blood vessel 3. As another example, it is also possible to consider a method in which a set of positions of the calculated intersections fall within the approximately fixed vicinity. For example, the center of the vicinity can be determined as the cross-sectional center position 4. When calculating the vicinity, a process of removing measurement errors can be introduced as a matter of course, such as setting a position range, in which about 80% of the set of positions of the intersections calculated are included, as the vicinity.

Functional Configuration

Figure 6:
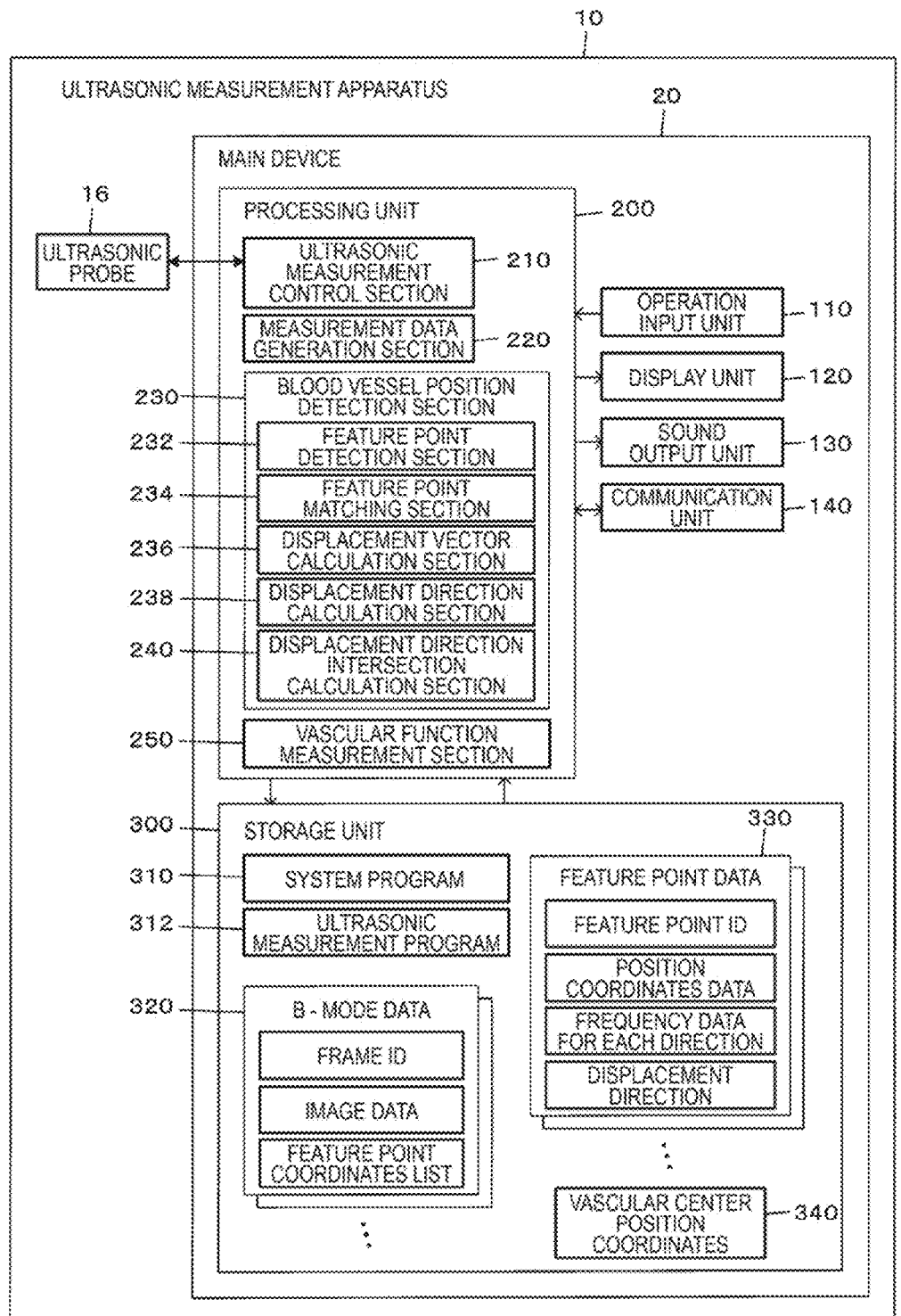
FIG. 6 is a diagram showing the functional configuration of the ultrasonic measurement apparatus.

FIG. 6 is a diagram showing the functional configuration of the ultrasonic measurement apparatus 10. As shown in FIG. 6, the ultrasonic measurement apparatus 10 includes an operation input unit 110, a display unit 120, a sound output unit 130, a communication unit 140, a processing unit 200, and a storage unit 300.

The operation input unit 110 is realized by an input device, such as button switches, a touch panel, or various sensors, and outputs an operation signal corresponding to an operation to the processing unit 200. In FIG. 1, the touch panel 12 or the keyboard 14 corresponds to the operation input unit 110.

The display unit 120 is realized by a display device, such as a liquid crystal display (LCD), and performs various kinds of display based on the display signal from the processing unit 200. In FIG. 1, the touch panel 12 corresponds to the display unit 120. The sound output unit 130 is realized by a sound output device, such as a speaker, and performs various kinds of sound output based on the sound signal from the processing unit 200.

The communication unit 140 is realized by a wireless communication device, such as a wireless local area network (LAN) or Bluetooth (registered trademark), or a communication device, such as a modem, a jack of a communication cable, or a control circuit, and is connected to a predetermined communication line to perform communication with an external device. In FIG. 1, the communication IC 28 mounted on the control board 22 corresponds to the communication unit 140.

The processing unit 200 is realized by a microprocessor such as a central processing unit (CPU) or a graphics processing unit (GPU), an application specific integrated circuit (ASIC), or an electronic component such as an integrated circuit (IC) memory. The processing unit 200 controls the operation of the ultrasonic measurement apparatus 10 by performing various kinds of arithmetic processing based on a program or data stored in the storage unit 300, an operation signal from the operation input unit 110, and the like. The processing unit 200 includes an ultrasonic measurement control section 210, a blood vessel position detection section 230, and a vascular function measurement section 250.

The ultrasonic measurement control section 210 controls the transmission and reception of an ultrasonic wave in the ultrasonic probe 16. Specifically, the ultrasonic measurement control section 210 performs control such that an ultrasonic wave is transmitted from the ultrasonic probe 16 at the transmission timing occurring at predetermined periods. In addition, the ultrasonic measurement control section 210 performs amplification or the like of a signal of the reflected wave of the ultrasonic wave received in the ultrasonic probe 16.

The measurement data generation section 220 generates measurement data including image data of each mode, such as an A mode, a B mode, or an M mode, based on the received signal of the reflected wave in the ultrasonic probe 16. The measurement data generation section 220 corresponds to a measurement data acquisition unit.

The blood vessel position detection section 230 includes a feature point detection section 232, a feature point matching section 234, a displacement vector calculation section 236, a displacement direction calculation section 238, and a displacement direction intersection calculation section 240, and detects a blood vessel position based on the measurement data generated by the measurement data generation section 220.

The feature point detection section 232 detects a feature point in a B-mode image in each measurement frame. In this case, the feature point detection section 232 detects a feature point that appears in each B-mode image during a predetermined period of time (for example, 1 to 2 seconds) and has a predetermined feature quantity or more, that is, a feature point whose position can be tracked.

The feature point matching section 234 performs matching of the feature points detected by the feature point detection section 232 between frames. Matching can be performed from the features on the image of each feature point (brightness value or surrounding brightness value of the feature point) or the like.

The displacement vector calculation section 236 calculates the displacement vector V of the feature points matched by the feature point matching section 234 between the respective frames.

The displacement direction calculation section 238 calculates a displacement direction of each feature point detected by the feature point detection section 232 from the displacement vector V calculated by the displacement vector calculation section 236. Specifically, the displacement direction calculation section 238 calculates the frequency of occurrence of the direction of the displacement vector V for each feature point, and determines the most frequently appearing direction as the displacement direction of the feature point. This displacement vector calculation section 236 and the displacement direction calculation section 238 correspond to a displacement detection unit.

The displacement direction intersection calculation section 240 calculates, for each feature point, a displacement direction line that passes through the position coordinates of the feature point and is in a direction along the displacement direction calculated by the displacement direction calculation section 238. Then, the displacement direction intersection calculation section 240 calculates an intersection between each feature point and a displacement direction line. A determination method when the number of intersections is not 1 is as described above. This intersection is detected as a cross-sectional center position of the blood vessel, and is stored as vascular center position coordinates 340 in the B-mode image.

The vascular function measurement section 250 performs measurement of predetermined vascular function information. Specifically, the vascular function measurement section 250 performs measurement of vascular function information, such as calculating the pulse rate, by measuring the IMT or the vessel diameter of a blood vessel specified by the detected blood vessel position or by estimating the blood pressure from the vessel diameter change by tracking the front and rear walls of the blood vessel.

The storage unit 300 is realized by a storage device, such as a ROM, a RAM, or a hard disk, and stores a program or data required for the processing unit 200 to perform overall control of the ultrasonic measurement apparatus 10. In addition, the storage unit 300 is used as a working area of the processing unit 200, and temporarily stores calculation results of the processing unit 200, operation data from the operation input unit 110, and the like. In FIG. 1, the storage medium 26 mounted on the control board 22 corresponds to the storage unit 300. In the present embodiment, an ultrasonic measurement program 312, B-mode data 320, feature point data 330, and the vascular center position coordinates 340 are stored in the storage unit 300.

The B-mode data 320 is generated for each measurement frame, and includes a frame ID, B-mode image data, and a feature point coordinates list that is a list of the position coordinates of each feature point in the B-mode image.

The feature point data 330 is generated for each feature point detected by the feature point detection section 232, and includes a feature point ID, position coordinates data that is the position coordinates in the B-mode image in each measurement frame, occurrence frequency data for each direction, and a displacement direction. The occurrence frequency data for each direction is data used by the displacement direction calculation section 238, and is data of the frequency of occurrence obtained by totaling the number of occurrences of the displacement vector V, which is calculated in each measurement frame by the displacement vector calculation section 236, for each direction. The occurrence frequency data for each direction can also be said to be data obtained by totaling the number of displacement vectors V in each measurement frame for each direction. In addition, data of the displacement vector V calculated in each measurement frame may be included in the feature point data 330.

Flow of the Process

Figure 7:
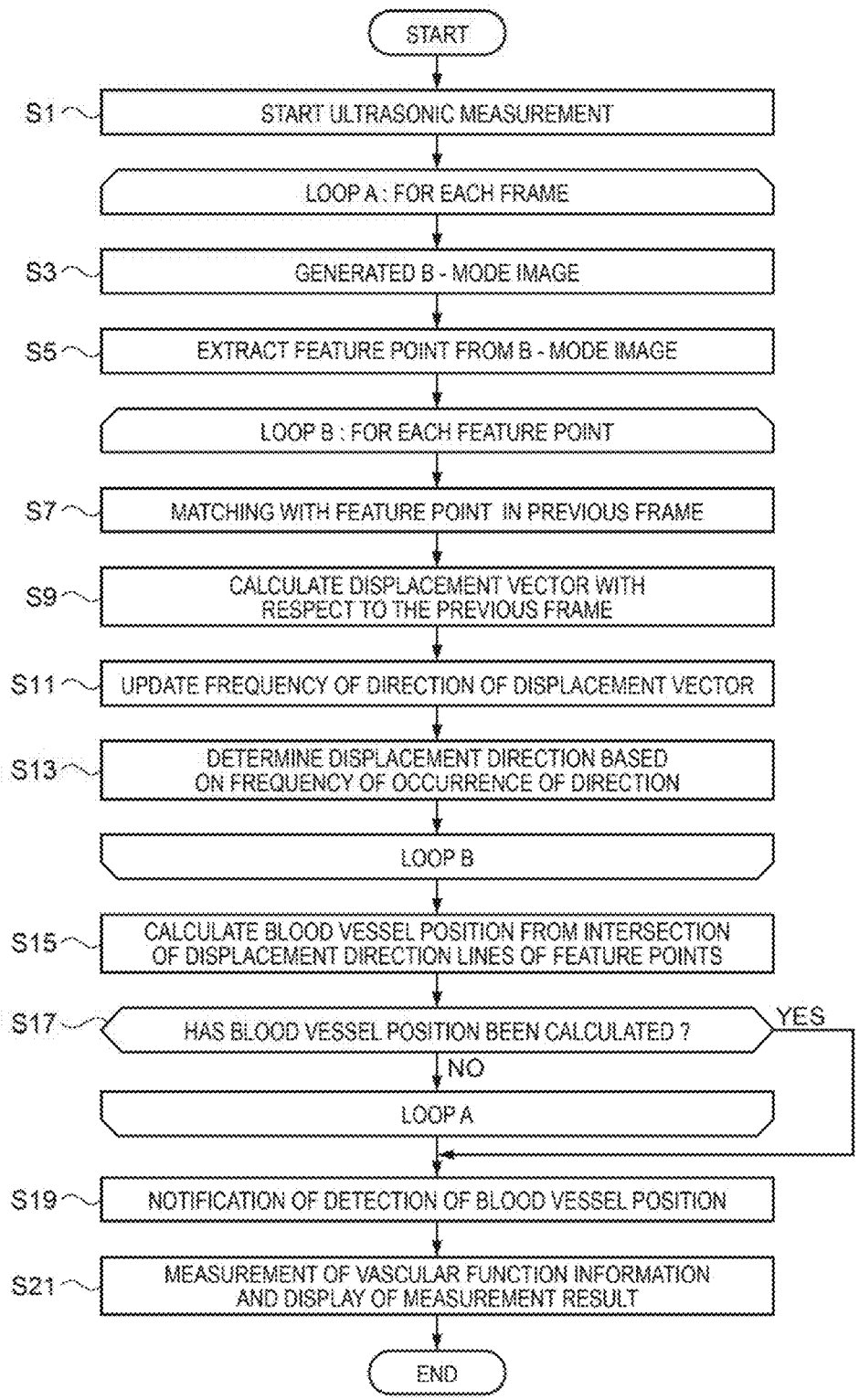
FIG. 7 is a flowchart of the ultrasonic measurement process.

FIG. 7 is a flowchart illustrating the flow of the ultrasonic measurement process. This process is realized by the execution of the ultrasonic measurement program. 312 by the processing unit 200.

First, the processing unit 200 starts the transmission and reception of an ultrasonic wave using the ultrasonic probe 16 (step S1). Then, the processing of loop A is repeated for each measurement frame. In loop A, the measurement data generation section 220 generates a B-mode image based on the received signal of the ultrasonic reflected wave in the ultrasonic probe 16 (step S3). Then, the feature point detection section 232 detects a feature point from the generated B-mode image (step S5).

Then, the process of loop B is performed for each detected feature point. In loop B, the feature point to be processed is matched with a feature point in the B-mode image in the previous frame (step S7), and the displacement vector V with respect to the previous frame is calculated (step S9). Then, in the occurrence frequency data for each direction included in the feature point data 330 of the feature point to be processed, the frequency of occurrence of the direction of the displacement vector V calculated in step S9 is updated (for example, "1" is added) (step S11). Then, the most frequently appearing direction in the data for each direction is determined as a displacement direction of the feature point to be processed (step S13).

The process of loop B is performed for all of the feature points. Then, the displacement direction line of each feature point is calculated and the intersection of the displacement direction lines is calculated, thereby the cross-sectional center position of the blood vessel being calculated (step S15). In this case, an intersection of the combination of every two displacement direction lines is calculated. However, when the coordinates of a predetermined number of intersections match each other (that is, when a predetermined number of displacement direction lines cross at one point (specifically, when a predetermined number of displacement direction lines pass through a predetermined narrow range)), the point of intersection is set as the cross-sectional center position of the blood vessel. If the cross-sectional center position of the blood vessel is not calculated (step S17: NO), the process of loop A is performed for the next measurement frame. When a long time has not passed from the start of measurement, a possibility of NO in step S17 is high since the occurrence frequency data for each direction includes few values. Then, if the cross-sectional center position of the blood vessel is calculated (step S17: YES), the process of loop A is ended.

After the process of loop A is ended, it is notified that the blood vessel position has been detected (step S19). Then, the vascular function measurement section 250 measures predetermined vascular function information using the ultrasonic wave transmission and reception results of the ultrasonic probe 16, and stores and displays the measurement results (step S21). After performing the processing described above, the ultrasonic measurement process is ended.

Effects

According to the present embodiment, the ultrasonic measurement apparatus 10 can calculate the displacement of each of a plurality of feature points from a plurality of time-series B-mode images acquired by ultrasonic measurement, and can detect an intersection between the displacement direction lines as the cross-sectional center position of the blood vessel. Therefore, it is possible to realize a new technique for detecting the blood vessel position to be subjected to ultrasonic measurement. In addition, since the technique is a relatively simple method of using the received signal of the reflected ultrasonic wave, the amount of arithmetic processing is small. Therefore, it is possible to increase the calculation speed.

Modification Examples

In addition, it should be understood that embodiments to which the invention can be applied are not limited to the embodiment described above and various modifications can be made without departing from the spirit and scope of the invention.

For example, the calculation of the displacement direction of each feature point based on the B-mode image may be performed in a period of either contraction or relaxation of the blood vessel. A blood vessel repeats contraction and relaxation according to the beating of the heart, and is displaced such that each feature point makes one round trip during one period of the contraction and relaxation. Therefore, it is possible to quickly detect the blood vessel position (cross-sectional center position) by detecting the displacement of the feature point in a period of either contraction or relaxation of the blood vessel.

The entire disclosure of Japanese Patent Application No. 2014-036406, filed on Feb. 27, 2014 is expressly incorporated by reference herein.

What is claimed is:

1. An ultrasonic measurement apparatus, comprising:
a measurement data acquisition unit that transmits an ultrasonic wave to a body and acquires measurement data, which is obtained by measuring a cross section of the body with the ultrasonic wave, based on a received signal; and
a processor configured to operate as:
a displacement detection unit that detects displacement of a tissue in the body based on the measurement data, wherein the displacement detection unit detects the displacement of the tissue in the body in synchronization with a periodic contraction and relaxation of a target blood vessel, the displacement of the tissue in the body being tissue around the target blood vessel and being detected using a B-mode image that is one type of measurement data; and
a blood vessel position detection unit that detects a cross-sectional center position of a blood vessel in the body based on the displacement of the tissue detected by the displacement detection unit.

2. The ultrasonic measurement apparatus according to claim 1,
wherein the displacement detection unit detects the displacement by comparing a plurality of pieces of measurement data in time series.

3. The ultrasonic measurement apparatus according to claim 1,
wherein the displacement detection unit detects a displacement direction of the tissue in the body, and
the blood vessel position detection unit detects the position of the blood vessel in the body based on the displacement direction.

4. The ultrasonic measurement apparatus according to claim 1, wherein the processor is further configured to operate as:
a feature point detection unit that detects feature points relevant to the tissue in the body based on the measurement data,
wherein the displacement detection unit detects displacement directions of the feature points, and
the blood vessel position detection unit detects the blood vessel position by calculating an intersection of lines of the displacement directions of the feature points.

5. The ultrasonic measurement apparatus according to claim 4,
wherein the feature point detection unit detects a feature point relevant to the blood vessel in the body or a tissue in the body at a location within a predetermined distance of the blood vessel in the body.

6. The ultrasonic measurement apparatus according to claim 1,
wherein the displacement detection unit detects the displacement according to at least one of contraction and relaxation of the blood vessel.

7. An ultrasonic measurement method, comprising:
transmitting an ultrasonic wave to a body and acquiring measurement data, which is obtained by measuring a cross section of the body with the ultrasonic wave, based on a received signal;
detecting displacement of a tissue in the body based on the measurement data and in synchronization with a periodic contraction and relaxation of a target blood vessel, the displacement of the tissue in the body being tissue around the target blood vessel and being detected using a B-mode image that is one type of measurement data; and
detecting a cross-sectional center position of a blood vessel in the body based on the displacement of the detected tissue.

* * * * *